US005643188A

United States Patent [19]

Oliveira

[11] Patent Number: 5,643,188

[45] **Date of Patent: *Jul. 1, 1997**

[54] LINER-PROTECTED ADHESIVE STRIP

[76] Inventor: Robert J. Oliveira, 200 Crestview Dr., Maplewood, Minn. 55119

[ * ] Notice: The portion of the term of this patent subsequent to Apr. 29, 2013, has been disclaimed.

[21] Appl. No.: 343,351

[22] Filed: Nov. 21, 1994

Related U.S. Application Data

[63] Continuation of Ser. No. 61,807, filed as PCT/US92/10231, Nov. 27, 1992, abandoned, which is a continuation-in-part of Ser. No. 803,576, Dec. 9, 1991, abandoned.

[51] Int. Cl.$^6$ .......................... B65D 73/00; A61F 13/00; A61B 19/02

[52] U.S. Cl. ................................ 602/54; 602/57; 602/58; 206/460; 206/441; 206/820

[58] Field of Search ............................ 602/52–59, 43–47; 128/849; 206/460, 441, 813, 820

[56] References Cited

U.S. PATENT DOCUMENTS

| | | | |
|---|---|---|---|
| 1,949,271 | 2/1934 | Duhamel | 206/441 X |
| 2,082,219 | 6/1937 | Scholl | 602/58 X |
| 2,563,689 | 8/1951 | Muhlhauser | 206/460 |
| 2,973,859 | 3/1961 | Schladermundt | 206/441 |
| 4,646,731 | 3/1987 | Brower | 128/156 |
| 4,781,293 | 11/1988 | Johns | 602/57 X |
| 4,807,613 | 2/1989 | Koehnke et al. | 128/155 |
| 5,052,381 | 10/1991 | Gilbert et al. | 128/155 |

FOREIGN PATENT DOCUMENTS

| | | | |
|---|---|---|---|
| 1327045 | 8/1973 | United Kingdom | 206/460 |

*Primary Examiner*—Danton D. DeMille
*Attorney, Agent, or Firm*—Richard E. Brink

[57] ABSTRACT

A strip of adhesive-coated sheet material is made easier to apply, even with one hand, if one end of the strip is mounted on a sheet release liner and the other end is mounted on one wing of a folded release liner.

10 Claims, 3 Drawing Sheets

LINER-PROTECTED ADHESIVE STRIP

CROSS-REFERENCE TO A RELATED APPLICATION

This is a continuation of application Ser. No. 08/061,807, filed as PCT/US92/10231, Nov. 27, 1992, now abandoned, which is a continuation-in-part of application Ser. No. 07/803,576, Dec. 9, 1991, now abandoned.

BACKGROUND OF THE INVENTION

This invention relates to strips of sheet material at least partially coated with normally tacky and pressure-sensitive adhesive (PSA) and mounted on a removable liner.

PSA-coated strips are well-known and are widely used for a variety of purposes. One common example is the familiar strip bandage, which is used to protect small wounds. Other examples include the coded adhesive strips that are wrapped around electrical wires or cables for identification purposes, return address labels, corn plasters, transdermal patches, decals, year tabs for automobile license plates, transparent labels for graphics, nose pads for spectacles, and, in more recent times, wax guards for applying over the sound-transmitting tube of hearing aids. Useful as all of these PSA-coated strips are for their intended purpose, it is sometimes difficult to apply them, especially if the strips are small enough to be applied using only one hand (e.g., 1 cm×2.5 cm) and even more difficult if only one hand can be used to remove the strip from a protective liner and apply it in a desired location. This difficulty is also directly related to the aggressiveness of the PSA. Prior to the present invention, it is believed that no satisfactory solution to this problem has been available.

BRIEF SUMMARY

The present invention provides, as a new article of manufacture, a pressure-sensitive adhesive-coated strip that is especially adapted for being applied in a desired location using only one hand. The strip has first and second end portions, the adhesive at the first end portion being in contact with a sheet of release liner and the adhesive at the second end portion being in contact with the second wing of a folded release liner having first and second wings, the first wing being longer than the second wing and extending beyond both the second wing and the second end portion of the adhesive-coated strip. This novel construction permits a user to grip the distal portion of the first wing and lift it so as to peel the first end portion of the adhesive-coated strip from the release liner sheet and apply it to a first desired location. The user can then pull on the distal portion of the first wing to peel the second wing of the folded release liner from the second end portion of the adhesive-coated strip and apply the second end portion to a second desired location.

BRIEF DESCRIPTION OF THE DRAWING

Understanding of the invention will be facilitated by referring to the accompanying drawing, in which like numbers refer to like pads in the several views and in which.

DETAILED DESCRIPTION

For convenience, the invention will now be described in more detail in relation to a particular type of adhesive-coated sheet material, viz., a cerumen (ear wax) guard for installation over the sound outlet port of hearing aids. A wax guard of this type may comprise a strip of sheet material, at least each end portion of which is coated with normally tacky and pressure-sensitive adhesive, the central portion of the strip being provided with a sound-transmitting, wax-entrapping material that is positioned over the sound outlet port of a sound-transmitting device, especially a hearing aid, the PSA-coated end portions contacting the housing surrounding the sound-transmitting tube and holding the guard in its desired location. Such guards are described in more detail in aforementioned copending parent application Ser. No. 07/803,576, the disclosure of which is incorporated herein by reference.

Figure 1:
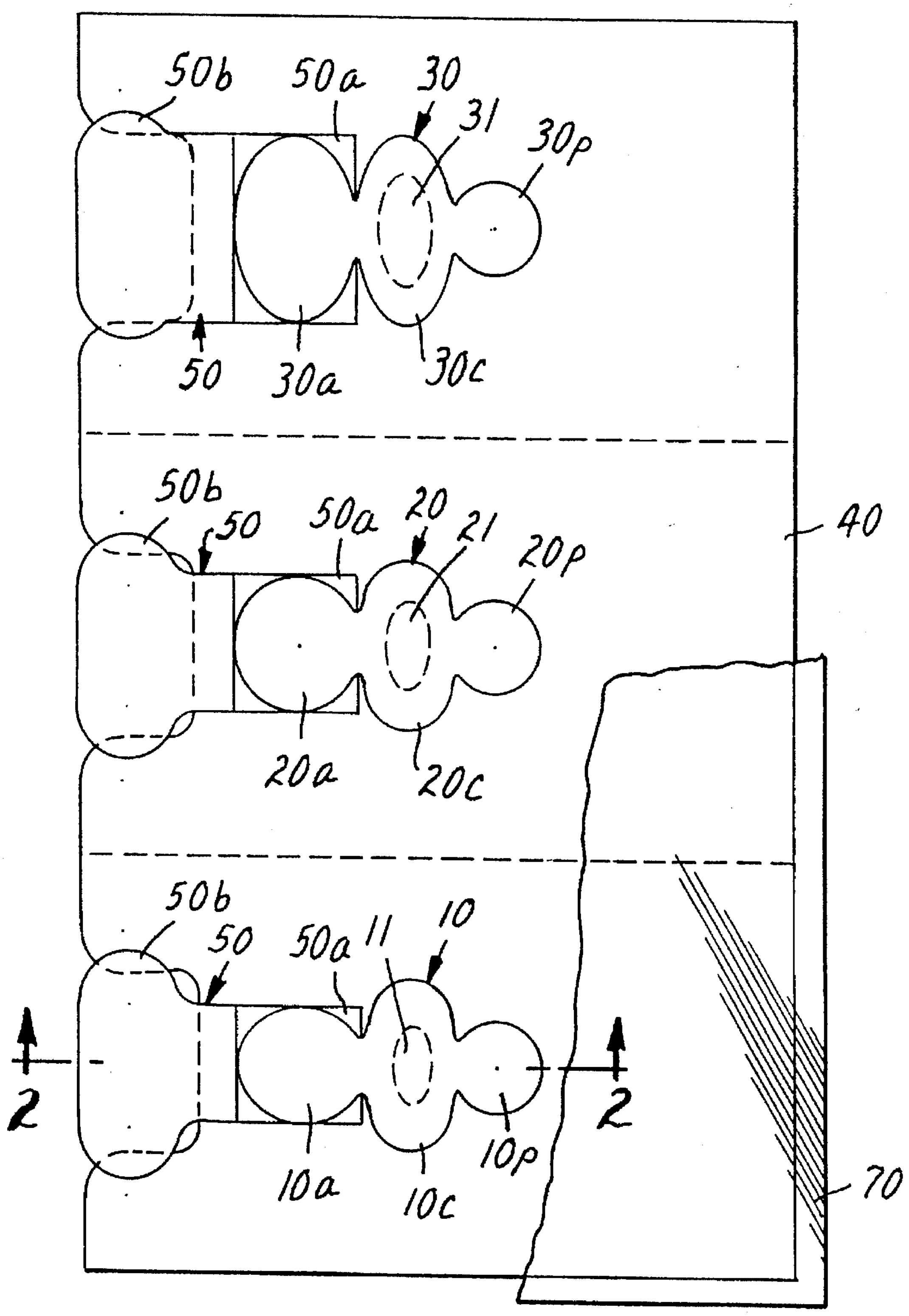
FIG. 1 is a greatly enlarged plan view of a currently preferred embodiment of the invention, showing three PSA-coated wax guards of different dimensions, with one attaching lobe of each positioned on a sheet release liner and the other attaching lobe of each positioned on a folded release liner.
Figure 2:
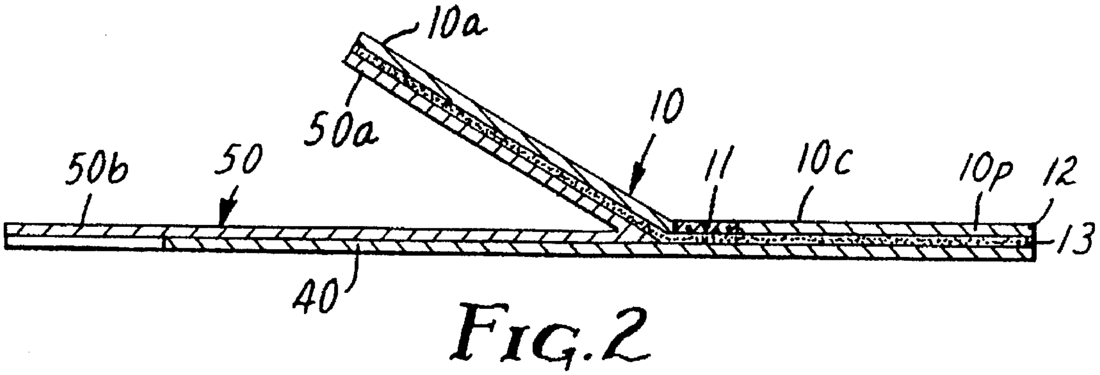
FIG. 2 is a cross-sectional view of the assembly shown in FIG. 1, taken along section line 2—2, looking in the direction of the arrows.
Figure 3:
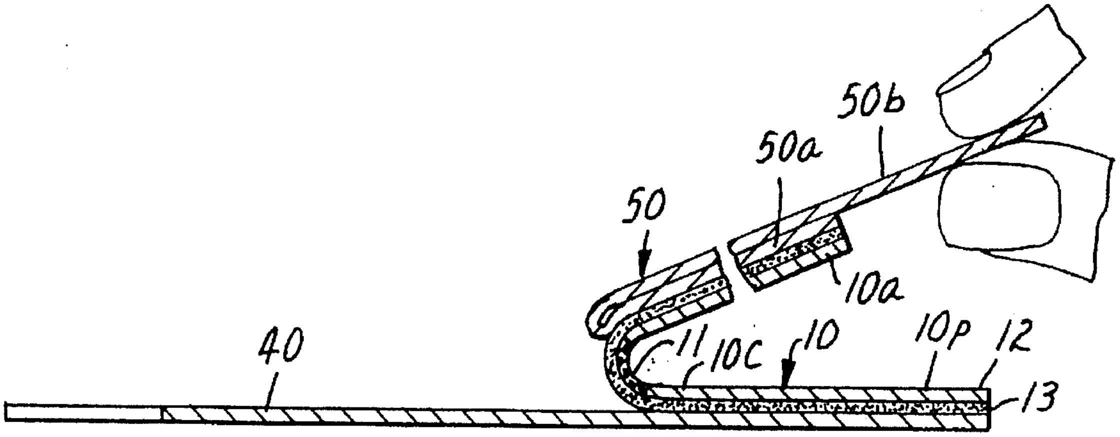
FIG. 3 depicts the initial step in removing the wax guard from the sheet liner.
Figure 4:
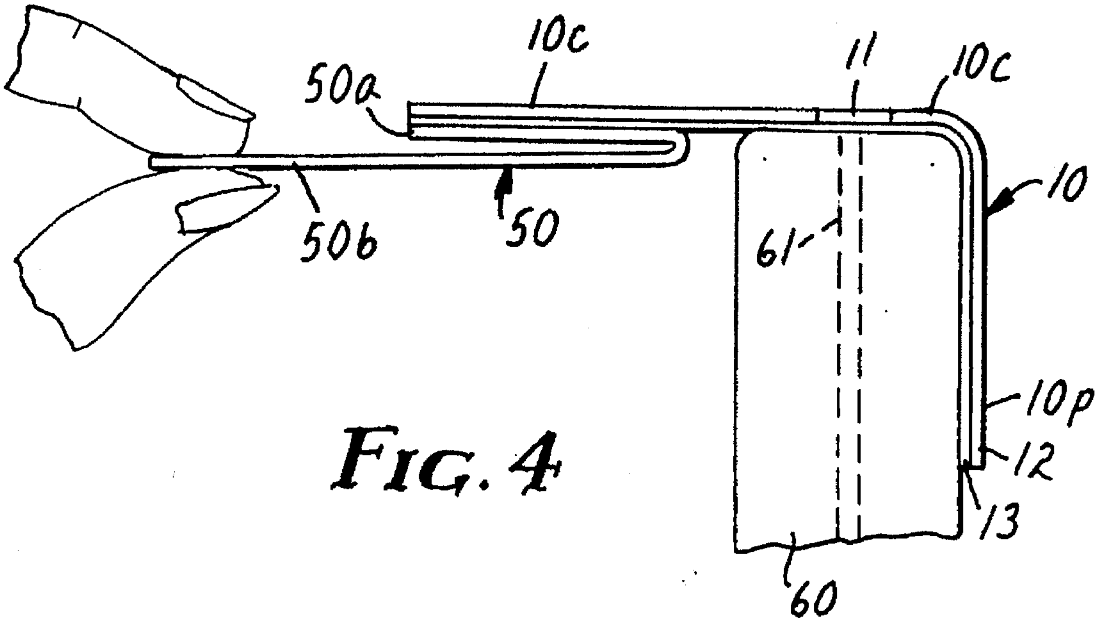
FIG. 4 shows the process of adhering the exposed lobes of the wax guard to a highly stylized portion of the housing of a hearing aid.
Figure 5:
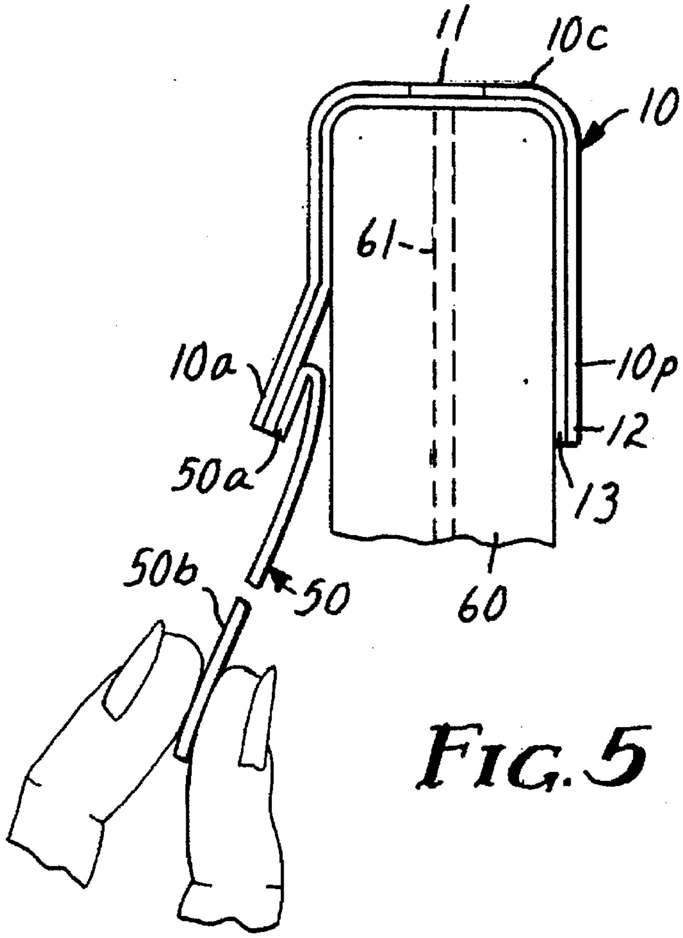
FIG. 5 shows the technique for removing the folded release liner from the other lobe of the wax guard and applying this lobe to the housing of a hearing aid.

In the drawings, FIG. 1 depicts the manner in which wax guards can be mounted for distribution to hearing aid dispensers or wearers of hearing aids. Three wax guards, 10, 20, 30 are shown, each having a first end portion, or lobe, **10*p*, 20*p*, 30*p*, a second end portion, or lobe, 10*a*, 20*a*, 30*a*, and a central portion, or lobe 10*c*, 20*c*, 30*c*, which is provided with a sound-transmitting but wax-entrapping portion 11, 21, 31. The adhesive-coated surface of lobes 10*p*, 20*p*, 30*p* and central lobes 10*c*, 20*c*, 30*c* are in contact with the release surface of sheet liner 40. The adhesive-coated surface of lobes 10*a*, 20*a*, 30*a* are not in contact with sheet liner 40 but instead are in contact with folded release liner 50; this folded liner 50 comprises first wing 50*b* and second wing 50*a*, the adhesive-coated surface of lobes 10*a*, 20*a*, 30*a* being in contact with wing 50*a*. Wing 50*b* extends beyond the end portion of lobes 10*a*, 20*a*, 30*a*, as well as beyond the end portion of wing 50*a*. For the convenience of a user in grasping wing 50*b*, the portion of sheet liner 40 underlying the distal end of wing 50*b*** is cut away and the said distal end is broadened.

Referring now to FIGS. 2–5, the manner of removing and attaching wax guard 10, comprising membrane 12, pressure-sensitive adhesive coating 13, and sound-transmitting, wax-entrapping portion 11, will be described in more detail. First, the user grasps the distal portion of wing **50*b* between a thumb and forefinger, lifts this distal portion and peels lobes 10*c* and 10*p* away from sheet liner 40. Next, while still gripping the distal portion of wing 50*b*, the user positions central lobe 10*c* so that wax-entrapping material 11 is positioned over sound outlet port 61 of hearing aid housing 60. Next, the adhesive-coated surface of lobe 10*p* is adhered to housing 60 in a desired first location. Then, while pulling on the distal portion of wing 50*b*, the user brings the adhesive-coated surface of lobe 50*a* into contact with the desired second location on the hearing aid housing while gradually stripping away wing 50*a* of folded release liner 50**. Although, of course, both hands can be used, it will be noted that the entire operation of removal and attachment can be carried out using only one hand.

To help make certain that wing **50*a* of folded release liner 50 is not prematurely released from lobe 10*a*, various modifications can be made. For example, the release surfaces of either sheet liner 40 or folded liner 50 can be treated so that the adhesion to sheet liner 40 is less than to folded liner 50. For the same reason, it is desirable for folded liner 50 to be formed of material which provides a minimum angle between wings 50***a* and 50*b*. Increasing the width of folded liner 50 also reduces the likelihood of premature separation of wing 50*a* from the adhesive-coated surface 13 of lobe 10*a* as lobes 10*c* and 10*p* are being peeled from liner 40. Premature separation is further minimized by ensuring that the angle between wings 50*a* and 50*b* of folded release liner 50 is kept as small as possible.

It may be helpful to bear in mind that the shear force applied to adhesive 13 on lobe 10*a* should be greater than the force required to peel lobe 10*p* from sheet liner 40. Similarly, after lobes 10*c* and 10*p* have been adhered to housing 60, the shear force exerted on the adhesive bonded to housing 60 should exceed the peel force applied to the adhesive-coated surface of lobe 10*a* during removal of wing 50*a* of folded release liner 50. It has been found that a silicone-coated densified kraft paper about 80 micrometers thick and weighing about 100 g/m makes an excellent material for forming a folded release liner.

Although, for convenience, the foregoing description relates to a wax guard for hearing aids, it is apparent that the same principles and application procedures will be effective with other PSA-coated strip material, especially where only one hand is available. For example, where an individual wishes to apply a strip bandage to one of his/her hands, it will be very helpful to have a bandage-liner construction that can be applied with his/her other hand. Surgeons, medical technicians, and nurses will also find that, if linered in the way described above, suture strips can be precisely positioned across the opposed edges of a wound incision and conveniently applied to hold the edges together. In this regard, it will be noted that wing 50*b* allows controlled placement of strip 10 while avoiding contamination and undesirable contact by the applier. Analogous applications will readily occur to those having a need to apply adhesive strips of various types.

As indicated in FIG. 1, adhesive-coated strips can be packaged and distributed in a transparent plastic envelope 70, which will help ensure that the products do not become prematurely detached from either sheet liner 40 or folded liner 50. It is contemplated that a kit containing a plurality of wax guards having a variety of thicknesses or sizes of attaching lobes may be desirable. It will similarly be recognized that any type of PSA-coated strip could be packaged in the same manner.

Those skilled in the art will immediately recognize that numerous variations of the invention can be made without departing from the spirit of what is disclosed. For example, the release liner sheet can be either a planar sheet, as shown, or, alternatively, an elongate strip wound convolutely upon itself in coil form, a plurality of adhesive-coated strips being spaced along its length.

What is claimed is as follows:

1. As a new article of manufacture, a pressure-sensitive adhesive-coated strip having first and second end portions, the adhesive at the first end portion being in contact with sheet of release liner and the adhesive at the second end portion being in contact with the second wing of a folded release liner having ends with a single fold therebetween forming first and second wings, the first wing extending beyond both the second wing of the folded release liner and the second end portion of the adhesive-coated strip, the folded release liner overlying the sheet release liner, the sheet release liner and the folded release liner being treated so that the adhesion of the adhesive-coated strip to the folded release liner is greater than the adhesion of the adhesive-coated strip to the sheet release liner, whereby a user can grip the distal portion of the first wing and lift it so as to peel the first end portion of the adhesive-coated strip from the sheet release liner, apply said first end portion to a first desired location, and then pull on said distal portion to peel the folded release liner from the second end portion of the adhesive-coated strip and apply the second end portion to a second desired location.

2. The article of claim 1 wherein the adhesive-coated strip is small enough to be applied conveniently using only one hand.

3. The article of claim 2 wherein the adhesive-coated strip is no larger than 1 cm×2.5 cm.

4. The article of claim 2 wherein the adhesive-coated strip is a sound-transmitting and wax-entrapping guard for mounting over the sound transmitting tube of a hearing aid.

5. The article of claim 1 wherein the distal portion of the first wing of the folded release liner is wider than the remainder of the folded release liner.

6. The article of claim 5 wherein said distal portion is positioned so as to overlie the sheet liner adjacent one edge thereof.

7. A method of applying the adhesive-coated strip of claim 1 to a desired location, allowing the use of only one hand, comprising the steps of (a) gripping the distal portion of the first wing of the folded release liner, (b) lifting the first wing of the folded release liner and the second end portion of the adhesive-coated strip, (c) peeling the first end portion of the adhesive-coated strip from the release liner sheet, (d) applying said first end portion to a desired first location, (e) pulling on said distal portion to peel said second wing from said second end portion, and (f) applying said second end portion to a desired second location.

8. As a new article of manufacture, a pressure-sensitive adhesive-coated strip having first and second end portions, the adhesive at the first end portion being in contact with a sheet of release liner and the adhesive at the second end portion being in contact with the second wing of a folded release liner having first and second wings, the first wing extending beyond both the second wing of the folded release liner and the second end portion of the adhesive-coated strip, the distal portion of said first wing overlying the sheet liner adjacent one edge, a portion of the edge of the sheet liner that said distal portion overlies is cut out so as to permit easier gripping of said distal portion, whereby a user can grip said distal portion of the first wing and lift it so as to peel the first end portion of the adhesive-coated strip from the release liner sheet, apply said first end portion to a first desired location, and then pull on said distal portion to peel the folded release liner from the second end portion of the adhesive-coated strip and apply the second end portion to a second desired location.

9. The article of claim 8 wherein the pressure-sensitive coated strip is a wax guard for an in the ear hearing aid.

10. As a new article of manufacture, a plurality of separate pressure-sensitive adhesive-coated strips spaced from each other, each having first and second end portions, the adhesive at the first end portion of each of said strips being in contact with the same sheet of release liner and the adhesive at the second end portion of each strip being in contact with the second wing of a separate folded release liner having ends with a single fold therebetween forming first and second wings, the first wing extending beyond both the second wing of the folded release liner and the second end portion of the adhesive-coated strip, the folded release liner overlying the sheet release liner, the sheet release liner and the folded release liner being treated so that the adhesion of the adhesive-coated strip to the folded release liner is greater than the adhesion of the adhesive-coated strip to the sheet release liner whereby a user can grip the distal portion of the first wing and lift it so as to peel the first end portion of an adhesive-coated strip from the sheet release liner, apply said first end portion to a first desired location, and then pull on said distal portion to peel the folded release liner from the second end portion of the adhesive-coated strip and apply the second end portion to a second desired location.

* * * * *